United States Patent [19]

Warriner

[11] Plant 5,002

[45] Mar. 22, 1983

[54] ROSE PLANT 75-21023—JACUM

[75] Inventor: William A. Warriner, Tustin, Calif.

[73] Assignee: Jackson & Perkins Company, Medford, Oreg.

[21] Appl. No.: 299,980

[22] Filed: Sep. 8, 1981

[51] Int. Cl.[3] ..... A01H 5/00

[52] U.S. Cl. ..... Plt./27

[58] Field of Search ..... Plt./22, 27

*Primary Examiner*—Robert E. Bagwill

*Attorney, Agent, or Firm*—Klarquist, Sparkman, Campbell, Leigh, Whinston & Dellett

[57] ABSTRACT

A floribunda rose variety having unusual red-purple color, clustered blooming on short stems, glossy foliage and strong fragrance.

1 Drawing Figure

1

This present invention relates to a new and distinct variety of rose plant of the floribunda class which was originated by me by crossing the variety White Masterpiece, U.S. Plant Pat. No. 2,998, with the variety Heirloom, U.S. Plant Pat. No. 3,234. The variety name, Jacum, has been given this variety.

The primary objective of this breeding was to produce a new rose variety combining the color of Heirloom with the bloom form and foliage of White Masterpiece. This objective was substantially achieved along with other desirable improvements as evidenced by the following unique combination of characteristics which are outstanding in the new variety and which distinguish it from its parents as well as from all other varieties of which I am aware:

1. A novel color in roses of R.H.S. Red Purple.
2. Strong fragrance.
3. Floribunda plant habit with flowers blooming in clusters on short stems.
4. Glossy, mildew resistant foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—White Masterpiece, U.S. Plant Pat. No. 2,998.

*Pollen parent.*—Heirloom, U.S. Plant Pat. No. 3,234.

Classification:

*Botanical.*—Rosa hybrid.

*Commercial.*—Floribunda.

FLOWER

Observations made from specimens grown outdoors at Irvine, Calif. in March.

2

Blooming habit: Continuous.

Bud:

*Size.*—1" to 1⅛" when petals start to unfurl.

*Form.*—Short, blunt top, broad base.

*Color.*—When sepals first divide, near Red-Purple 60C with some areas darkened to 60A or deeper. When half blown; upper side of petals near 60B; lower side of petals near 60B.

*Sepals.*—Color: Outer surface Green 138C with numerous stipitate glands. Three appendaged sepals lightly appendaged; two unappendaged sepals hairy edged.

*Receptacle.*—Color: Green 138B. Shape: Funnel. Size: Large. Surface: Smooth, glandular.

*Peduncle.*—Length: Short. Surface: Glandular. Color: Light green. Strength: Stiff, erect.

*Opening.*—Petals curl outward.

Bloom:

*Size.*—Large. Average open size is 8–10 cm.

*Borne.*—In clusters, flat.

*Stems.*—Medium, strong.

*Form.*—When first open, flat. Permanence: Retains its form to the end.

*Petalage.*—Number of petals under normal conditions: 36–40.

*Color.*—Center of flower: Upper side of petals, Red-Purple 60C; reverse side of petals, Red-Purple 60D; base of petals, near white. General tonality from a distance, Red-Purple 60C.

*Variegations.*—Occasional white streaks on midrib of outer petals.

*Discoloration.*—General tonality at end of first day, Red-Purple 60C; third day, Red-Purple 63C with irregular areas of 63B.

*Fragrance.*—Strong.

Petals:

*Texture.*—Thick.

*Shape.*—Round.

*Form.*—Tips slighty recurved.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large. Color: Yellow. Arrangement: Regular around styles.

*Filaments.*—Color: Red-Purple 63C.

*Pollen.*—Gold yellow.

*Styles.*—Color: Red-Purple 64A.
*Stigmas.*—Color: White.

PLANT

Form: Bush.
Growth: Vigorous, upright, branching.
Foliage: Number of leaflets on normal mid-stem leaves, 5.
*Size.*—Large.
*Quantity.*—Normal.
*Color.*—New foliage: Red-Purple 59A. Old foliage: Green 136A.
Leaflets:
*Shape.*—Oval pointed.
*Texture.*—Upper side: Glossy.
*Edge.*—Serrated.
*Serration.*—Single, small.
*Petiole.*—Rachis: Color: Reddish. Underside: Prickles.
*Stipules.*—Short.

*Disease resistance.*—Resistant to mildew under normal growing conditions at Irvine, Calif.
Wood:
*New wood.*—Color: Reddish. Bark: Smooth.
*Old wood.*—Color: Green. Bark: Smooth.
Prickles:
*Quantity.*—On main stalks from base, ordinary. On laterals from stalk, ordinary.
*Form.*—Small base, long, straight.
*Color when young.*—Brown.
*Position.*—Irregular.
Small prickles:
*Quantity.*—On main stalks, none. On laterals, none.

I claim:

1. A new and distinct variety of rose plant of the floribunda class, substantially as herein shown and described, characterized particularly as to novelty by the unique combination of its novel purple color, strong fragrance, floribunda habit and mildew resistant foliage.

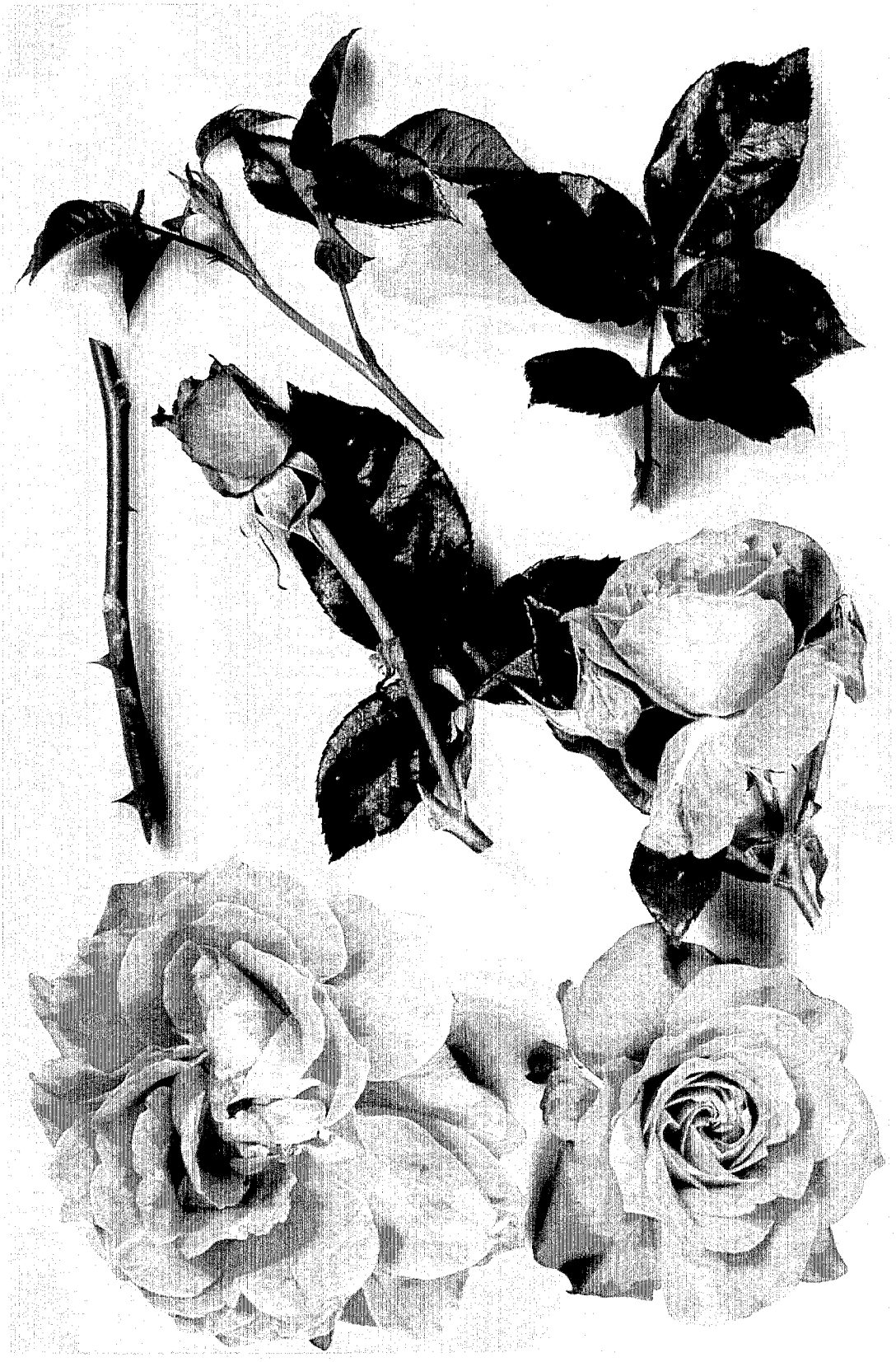

* * * * *